United States Patent
Kim et al.

(10) Patent No.: US 9,575,079 B2
(45) Date of Patent: Feb. 21, 2017

(54) APPARATUS AND METHOD FOR MEASURING CHOLESTEROL

(71) Applicant: LG Electronics Inc., Seoul (KR)

(72) Inventors: Jisu Kim, Seoul (KR); Seokjung Hyun, Seoul (KR); Yongju Yang, Seoul (KR); Kangsun Lee, Seoul (KR); Hyunho Oh, Seoul (KR); Guhan Kwon, Seoul (KR); Younjae Lee, Seoul (KR); Bongchu Shim, Seoul (KR); Gyoungsoo Kim, Seoul (KR); Dayeon Kang, Seoul (KR); Yonghyun Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 205 days.

(21) Appl. No.: 14/600,861

(22) Filed: Jan. 20, 2015

(65) Prior Publication Data

US 2015/0204811 A1 Jul. 23, 2015

(30) Foreign Application Priority Data

Jan. 21, 2014 (KR) .................. 10-2014-0007379
Jan. 9, 2015 (KR) .................. 10-2015-0003435

(51) Int. Cl.
*G01N 27/27* (2006.01)
*G01N 33/92* (2006.01)
*G01N 33/52* (2006.01)

(52) U.S. Cl.
CPC ............ *G01N 33/92* (2013.01); *G01N 33/526* (2013.01)

(58) Field of Classification Search
CPC .............................. G01N 33/92; G01N 33/526
See application file for complete search history.

(56) References Cited

U.S. PATENT DOCUMENTS

2014/0302611 A1* 10/2014 Orning ...................... B01L 3/02
436/71

* cited by examiner

*Primary Examiner* — Arun S Phasge
(74) *Attorney, Agent, or Firm* — Birch, Stewart, Kolasch & Birch, LLP

(57) ABSTRACT

Disclosed are an apparatus and a method for effectively measuring cholesterol using a small amount of blood. The apparatus for measuring cholesterol includes a cartridge where an upper case having a sample transferring membrane is movably coupled to a lower case having a sample measuring membrane; a cartridge accommodation unit configured to accommodate the cartridge therein; a memory configured to store therein setting information for sample measurement; and a controller configured to align the membranes of the upper case and the lower case with each other, by horizontally moving the lower case of the cartridge, according to the stored setting information, and configured to contact the membranes of the upper case and the lower case with each other, by vertically moving the upper case for sample transfer on each alignment position.

20 Claims, 15 Drawing Sheets

[FIRST POSITION(REFERENCE STATUS)]

[SECOND POSITION]

APPARATUS AND METHOD FOR MEASURING CHOLESTEROL

CROSS-REFERENCE TO RELATED APPLICATION

Pursuant to 35 U.S.C. §119(a), this application claims the benefit of earlier filing date and right of priority to Korean Application Nos. 10-2014-0007379 and 10-2015-0003435, filed on Jan. 21, 2014 and Jan. 9, 2015, the contents of which are incorporated by reference herein in their entireties.

BACKGROUND OF THE INVENTION

1. Field of the Invention

This specification relates to an apparatus and a method for measuring cholesterol, and more particularly, to an apparatus and a method for effectively measuring cholesterol using a small amount of blood.

2. Background of the Invention

As a population structure is changed into an aging society recently, concerns for health are increased. In such a situation, equipment of health diagnosis is highly required, and the equipment has a high possibility to be presented on a new market.

Generally, a patient's medical examination is performed by analyzing the patient's body fluid, and then by measuring the amount or concentration of a material (index material) included in the body fluid, the material related to the patient's health state such as disease or pregnancy. The index material is measured by extracting the patient's body fluid, and by performing a bio-chemical reaction such as an antigen-antibody reaction with respect to the index material. In the past, since an experimental drug or equipment requiring professional knowledge is used, high costs and longer time are required. Further, a patient should go to hospital for diagnosis. This may cause many restrictions to the patient.

In order to overcome such disadvantages, a point-of-care test (POCT) is being spotlighted. The POCT means a test for diagnosing a patient within a short time by immediately extracting a body fluid of the patient and analyzing the body fluid, on the spot where the patient is positioned.

The POCT is being widely used owing to its various advantages that a patient can perform self diagnosis in a simple manner, additional costs and time can be reduced, etc. Among such bio-chemical POCT items, cholesterol (TG, TC, HDL, LDL), blood sugar (Glucose) and a liver function (AST, ALT), etc. are much used. A biosensor for measuring such items is configured to perform its function using electrochemistry and optics (LED, PD).

An apparatus for measuring cholesterol applying optics (biosensor) uses a color-development reaction. In case of applying the biosensor using a color-development reaction, a solution itself may be used as a medium for moving or measuring fluid, or membranes may be used.

FIG. 1 is a schematic view illustrating an apparatus for measuring cholesterol in accordance with the conventional art.

As shown in FIG. 1, a user may insert a cartridge 20 into a cartridge accommodation unit (not shown) of an apparatus for measuring cholesterol 10, and then may inject blood into the cartridge 20 through a blood injection opening 12. Alternatively, the user may firstly injects blood into the cartridge 20, and then may insert the cartridge 20 into the cartridge accommodation unit.

FIG. 2 is a view illustrating a detailed structure of a cartridge inserted into the apparatus for measuring cholesterol.

As shown in FIG. 2, the conventional cartridge 20 includes an upper case 1 having a filtering membrane 1a and a spreading membrane 1b, and a lower case 3 having spreading membranes 3a and reaction membranes 3b. End portions of the upper case 1 and the lower case 3 are fixed to each other by an elastic member 2.

The filtering membrane 1a serves to transfer serum by filtering red blood cells (RBCs) from blood injected through the blood injection opening 12 of the apparatus. The spreading membrane 1b serves to spread the transferred serum. Especially, the spreading membrane 1b of the upper case 1 is a moving path of fluid, and a length thereof is the same as a distance between two membranes positioned at two ends of the lower case 3.

FIG. 3 is a view illustrating a cholesterol measuring operation using an apparatus for measuring cholesterol in accordance with the conventional art.

As shown in FIG. 3, if the cartridge 20 is inserted into the cartridge accommodation unit (not shown) of the apparatus for measuring cholesterol 10 and then blood is put to the cartridge 20 through the blood injection opening 12, serum of the blood, obtained after red blood cells (RBCs) are filtered by the filtering membrane 1a, is transferred to the spreading membrane 1b. Then, if the cartridge 20 is vertically moved by a driving means, the spreading membrane 1b of the upper case contacts the three spreading membranes 3a. As a result, the serum is transferred to three reaction membranes 3b from the spreading membrane 1b, through the three spreading membranes 3a. Then, the cartridge 20 is moved to the original position by the driving means. Then, light is projected onto the reaction membranes 3b by an optical unit (LED, PD), thereby checking a color-development reaction of the reaction membranes 3b. As a result, three types of cholesterol items (TC, TG, HDL) are simultaneously measured. The measured cholesterol level is displayed on a display unit.

In case of simultaneously measuring three types of cholesterol items (TC, TG, HDL) in the conventional apparatus for measuring cholesterol, in order to transfer serum obtained after red blood cells (RBCs) are filtered from blood, to the reaction membranes 3b, a moving path of liquid (serum), i.e., the spreading membrane 1b should be provided.

However, if the moving path of liquid is implemented as the spreading membrane 1b, a dead volume, a phenomenon that the spreading membrane 1b includes a large amount of fluid by absorption and spread of the fluid while the fluid flows, is generated.

As a result, a minimized amount of fluid for measuring cholesterol is not uniformly transferred to the reaction membranes 3b, or a small amount of fluid is transferred to the reaction membranes 3b, resulting in inaccurate measurement result values. Further, a larger amount of fluid (blood) should be used for a more precise measurement result values.

In the conventional apparatus for measuring cholesterol, blood reactions and processes according to each step are not separated from each other, but cholesterol items are measured through consecutive reactions. This may degrade process efficiency due to remaining fluid, fluid loss, interference between processes, etc. Especially, when a consecutive reaction processor is consecutively used, efficiency and performance according to each reaction step cannot be monitored. This may cause a failure rate of the entire system to be increased, and may cause a difficulty in actively controlling each step for enhanced efficiency according to each reaction step.

Further, in most of point of care test (POCT) equipment such as the conventional apparatus for measuring cholesterol, blood is taken by an additional subsidiary device for blood collection. Then, the collected blood is injected into a cartridge. Using such two steps may cause a user's inconvenience.

SUMMARY OF THE INVENTION

Therefore, an aspect of the detailed description is to provide an apparatus for measuring cholesterol, capable of reducing a dead volume occurring due to fluid flow, and a method thereof.

Another aspect of the detailed description is to provide an apparatus for measuring cholesterol capable of removing non-uniform serum distribution and deviation occurring due to a membrane path, and a method thereof.

Another aspect of the detailed description is to provide an apparatus for measuring cholesterol having a cartridge of a lamination membrane structure, capable of connecting and separating consecutive reactions of fluid in a physical manner, and a method thereof.

Another aspect of the detailed description is to provide an apparatus for measuring cholesterol capable of simplifying a blood collecting processor before blood analysis, and a method thereof.

To achieve these and other advantages and in accordance with the purpose of this specification, as embodied and broadly described herein, there is provided an apparatus for measuring cholesterol, including: a cartridge where an upper case having a sample transferring membrane is movably coupled to a lower case having a sample measuring membrane; a cartridge accommodation unit configured to accommodate the cartridge therein; a memory configured to store therein setting information for sample measurement; and a controller configured to align the membranes of the upper case and the lower case with each other, by horizontally moving the lower case of the cartridge, according to the stored setting information, and configured to contact the membranes of the upper case and the lower case with each other, by vertically moving the upper case for sample transfer on each alignment position.

In an embodiment, the cartridge may include: a body having a plate-shape and provided with a guide portion of a predetermined depth; a lower case inserted into the guide portion; and an upper case crossing the lower case above the lower case, and having two sides thereof fixed to the body by an elastic member, wherein the guide portion has the same shape as the lower case.

In another embodiment, the cartridge may include: an upper case having a pipe shape and forming a guide portion as a bottom surface thereof is cut into a predetermined size; an elastic member spaced from the guide portion, and attached to an inner side of the upper case; and a drawer-type lower case inserted to a space between the elastic member and the guide portion, and sliding back and forth along the guide portion.

To achieve these and other advantages and in accordance with the purpose of this specification, as embodied and broadly described herein, there is also provided a method of measuring cholesterol using a cartridge including an upper case having a plurality of sample transferring membranes, and a lower case having one or more sample measuring membranes, the method including: mounting a cartridge onto which a sample to be measured has been injected, to a cartridge accommodating unit; sequentially-aligning the membranes with each other by horizontally moving the lower case according to setting information, and contacting the membranes of the upper case and the lower case with each other by vertically moving the upper case, for transfer of the sample to be measured on each alignment position; measuring color-development information by projecting light onto the sample measuring membranes, while horizontally moving the lower case in a state where the contact state of the membranes has been released; and calculating a cholesterol level by analyzing the measured color-development information.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

Description will now be given in detail of preferred configurations of apparatuses for measuring cholesterol according to the present invention, with reference to the accompanying drawings.

The present invention proposes a method capable of reducing fluid loss due to fluid flow, by aligning and contacting membranes with each other, by moving an upper case (or upper portion) of a cartridge vertically, and by moving a lower case (or lower portion) of the cartridge horizontally.

Further, the present invention provides a method capable of preventing blood leakage by being provided with a capillary channel having a predetermined gradient for transferring blood to membranes, and capable of enhancing efficiency and performance of an apparatus for measuring cholesterol, by driving consecutive processes of a blood reaction in an active and distributed manner.

The present invention provides an apparatus for measuring cholesterol using an optical unit (biosensor), and the apparatus measures three items for measuring cholesterol (TC, TG, HDL) using membranes.

Figure 1:
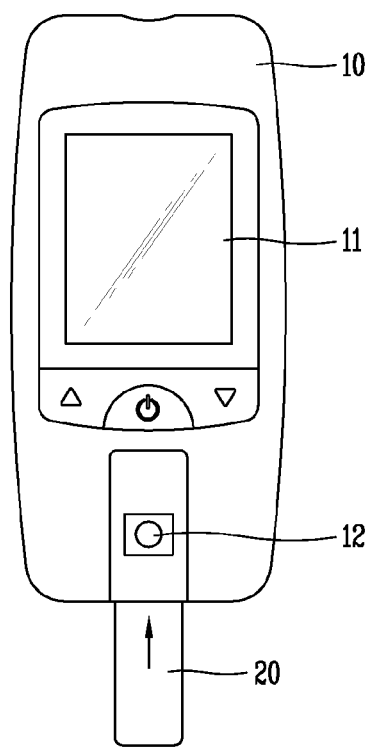
FIG. 1 is a view illustrating appearance of an apparatus for measuring cholesterol in accordance with the conventional art.
Figure 2:
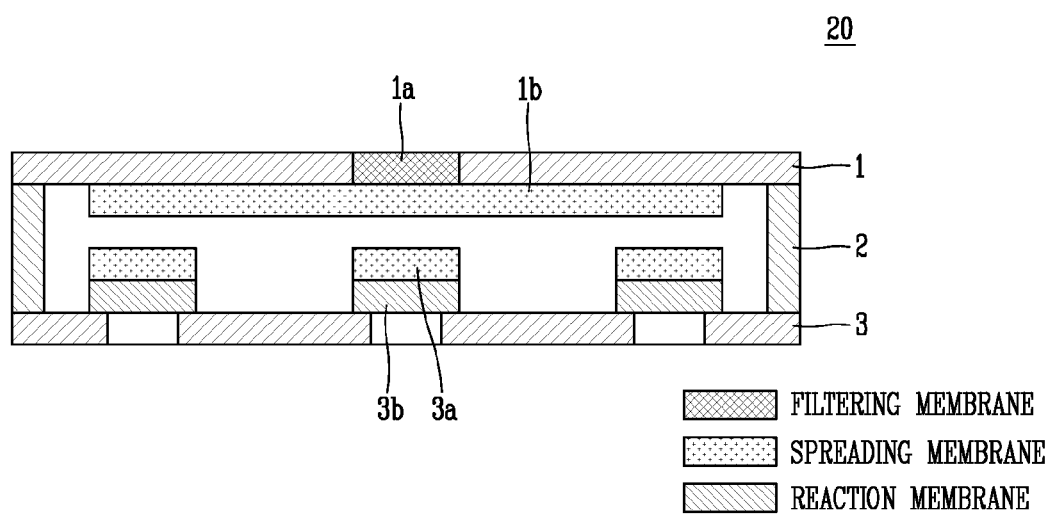
FIG. 2 is a view illustrating a detailed structure of a measuring cartridge inserted into an apparatus for measuring cholesterol.
Figure 3:
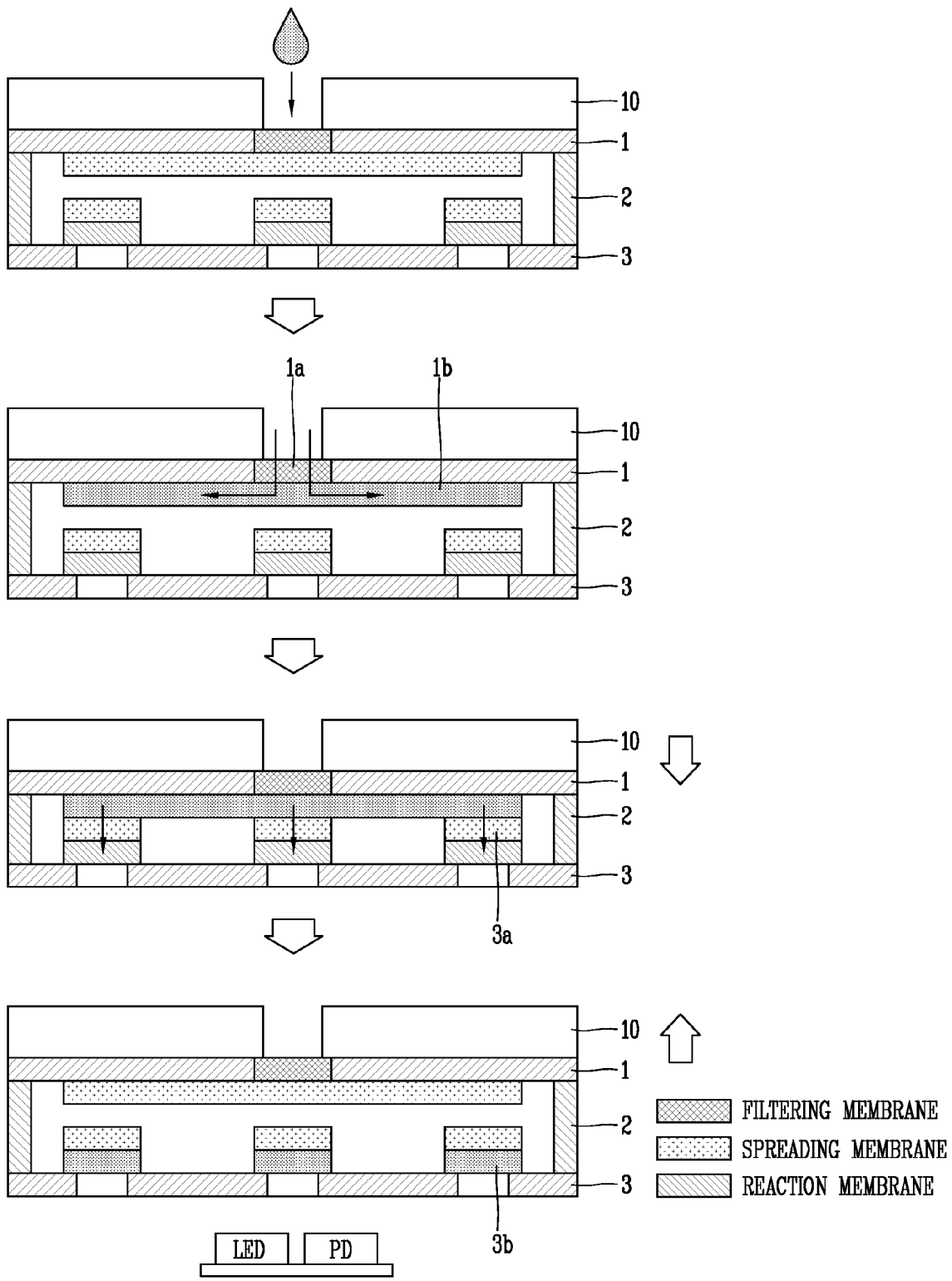
FIG. 3 is a view illustrating a cholesterol measuring operation using an apparatus for measuring cholesterol in accordance with the conventional art.
Figure 4:
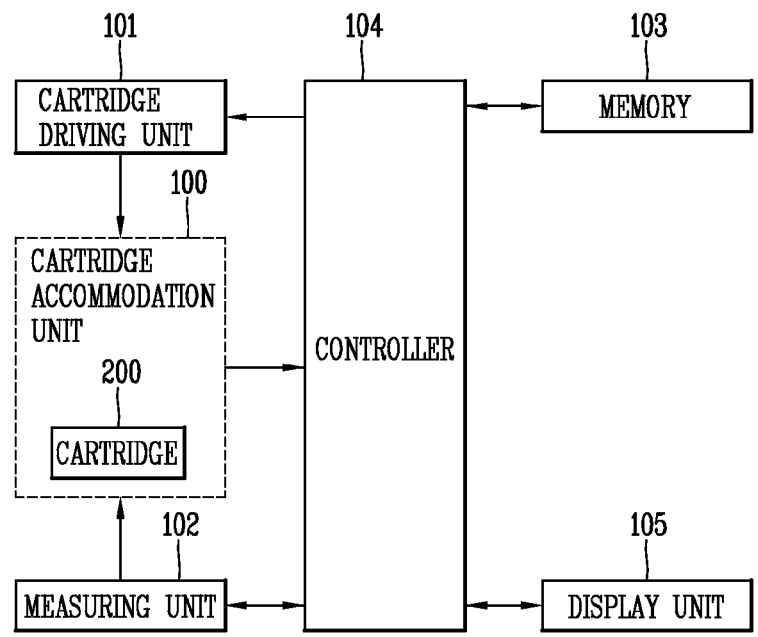
FIG. 4 is a view illustrating a configuration of a blood analyzing cartridge according to a first embodiment of the present invention.

FIG. 4 is a block diagram of an apparatus for measuring cholesterol according to the present invention.

As shown in FIG. 4, the apparatus for measuring cholesterol includes a cartridge accommodation unit 100 configured to accommodate a cartridge 200 therein; a cartridge driving unit 101 configured to control horizontal and vertical movements of the cartridge 200 in the cartridge accommodation unit 100; a measuring unit 102 configured to detect color-development information by projecting an optical signal onto reaction membranes of the cartridge 200; a memory 103 configured to store therein setting information for measuring the color-development information, and to store therein a measured cholesterol level; a controller 104 configured to control an operation of each component, and to calculate a cholesterol level (a result value on concentration measurement) by processing the color-development information detected by the measuring unit 102; and a display unit 105 configured to display a cholesterol level measured by the controller 104.

The setting information for measuring the color-development information is information settable by a user, which may include a membrane initial alignment position, a membrane contact time, cholesterol measuring items, horizontal and vertical moving distances of a membrane. Under an assumption that the number of measuring items is two, only two membranes of a lower case 26 shown in FIG. 5 may contact two membranes of the upper case 21, and color-development information may be measured.

The cartridge accommodation unit 100 may be attached to one of a lower surface, an upper surface and a side surface of the apparatus.

The measuring unit 102 includes an LED configured to output an optical signal to a reaction membrane of the cartridge 200, a photo diode (PD) configured to detect an optical signal reflected from a reaction membrane of the LED, and a signal process module configured to select a required image from the detected optical signal and to transmit the selected image to the controller 104.

The cartridge driving unit 101 includes a vertical movement motor configured to vertically move the upper case of the cartridge 200, and a horizontal movement motor configured to horizontally move the lower case. The cartridge driving unit 101 serves to precisely align a membrane of the upper case with each membrane of the lower case.

The controller 104 may include a control module for driving each motor of the cartridge driving unit 101, a control module for controlling the measuring unit 102, an ND converter and a signal processing module for converting color-development information detected by the measuring unit 102 into digital information and processing the converted color-development information, and a concentration extraction module for finally measuring a cholesterol level.

Figure 5:
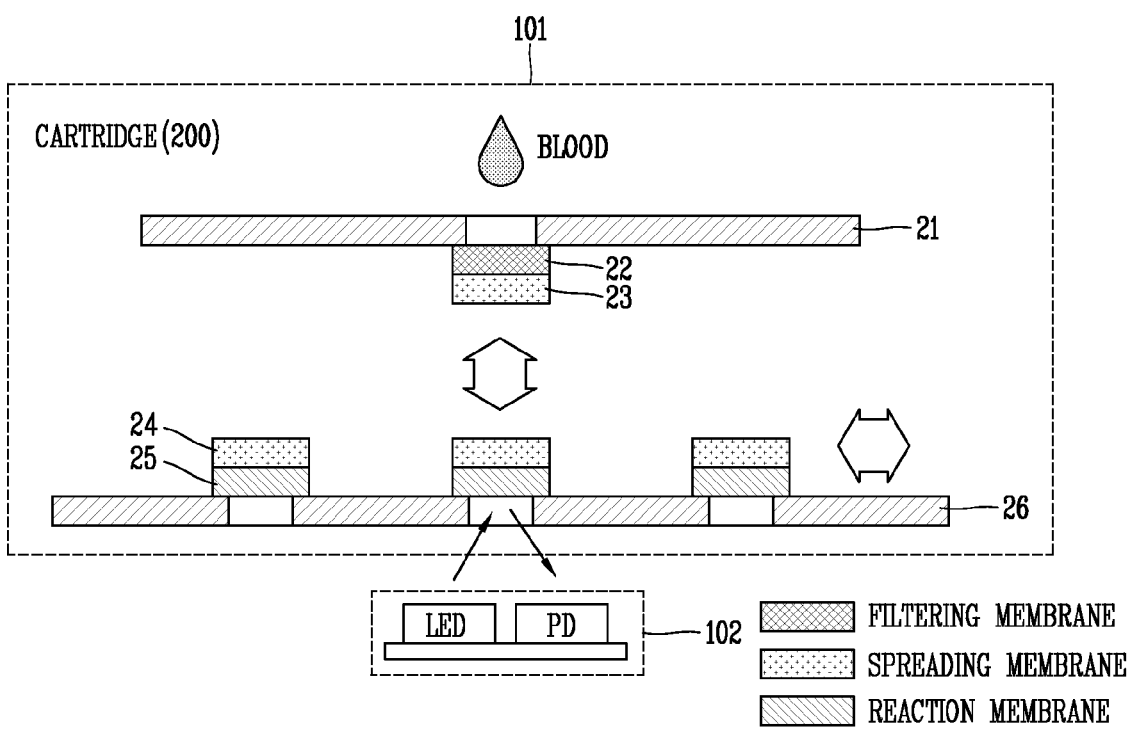
FIG. 5 is a block diagram of an apparatus for measuring cholesterol according to the present invention.
Figure 6:
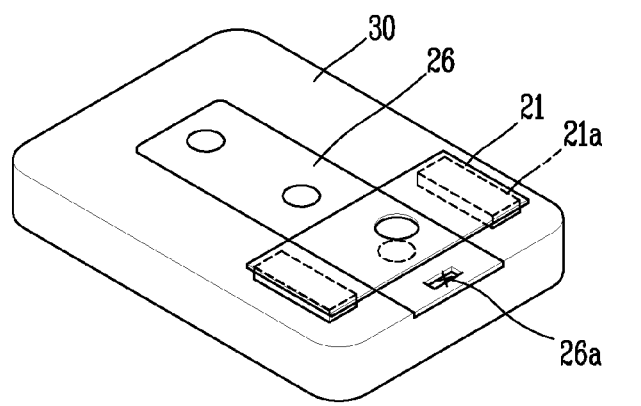
FIG. 6 is view a illustrating a configuration of a cartridge according to a first embodiment of the present invention.
Figure 6:
Figure 6:
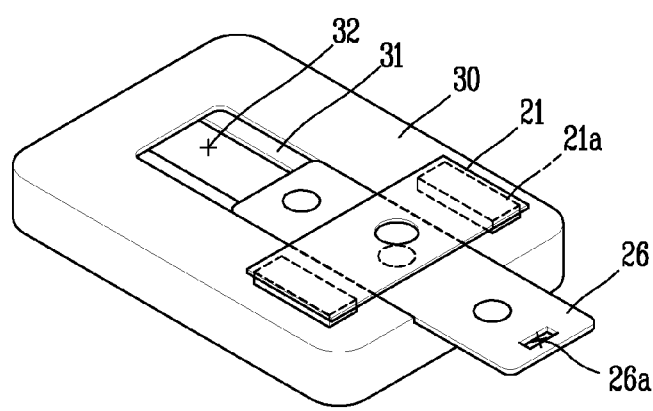
Figure 6:
Figure 6:
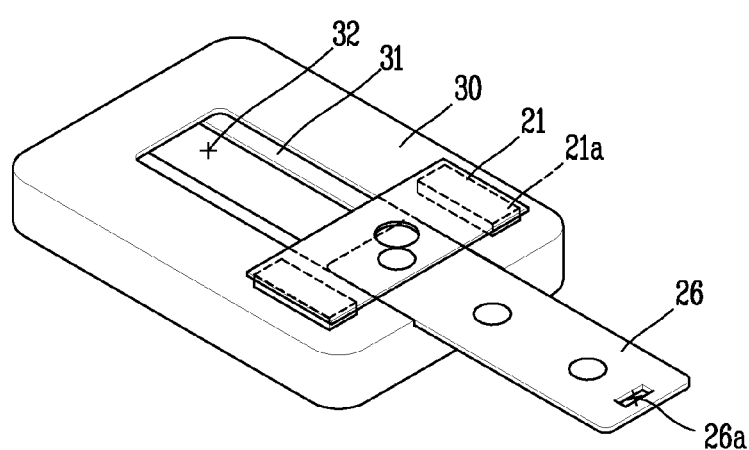

FIGS. 5 and 6 are views illustrating a configuration of the cartridge 200 according to a first embodiment of the present invention.

As shown in FIGS. 5 and 6, the cartridge 200 of the present invention includes a body 30 having a plate-shape and provided with a guide portion (or guide region) of a predetermined depth, a lower case 26 having one or more sample measuring membranes and inserted into the guide portion, and an upper case 21 having a plurality of sample transferring membranes, crossing the lower case 26 above the lower case 26, and having two sides thereof fixed to the body 30 by an elastic member.

The guide portion has the same shape as the lower case 26.

The upper case 21 may include a filtering membrane 22 and a spreading membrane 23, and the lower case 26 may include reaction membranes 25 through spreading membranes 24. In another embodiment, the lower case 26 may include only reaction membranes.

The filtering membrane 22 filters red blood cells (RBCs) from blood injected through a blood injection opening (not shown) of the apparatus, thereby transferring a serum. The spreading membranes 23, 24 serve to spread the transferred serum.

The reaction membranes 25 are provided with a reaction layer with respect to cholesterol measuring items, i.e., total cholesterol (TC), triglyceride (TG), and high-density lipoprotein (HDL), thereby having a color-development reaction with respect to light.

The upper case 21 is attached to the body 30 by an elastic member 21a, such that it is positioned at a predetermined height to cross the lower case 26. As shown in FIG. 6, the elastic member 21a is positioned between a bottom surface of the upper case 21 and an upper surface of the body 30, thereby fixing the upper case 21 to the body 30. The elastic member 21a is contracted when the upper case 21 is vertically moved, thereby contacting membranes of the upper case 21 and the lower case 26 with each other.

A predetermined region 32 of the body 30 is cut so that the lower case 26 can be inserted thereinto with a predetermined depth. Two sides of the cut surface are bent in an 'L'-shape, thereby forming a guide portion 31 for guiding horizontal movement of the lower case 26. The lower case 26 is formed at the same height or at a higher height as/than a horizontal surface of the body 30.

A driving hole 26a is provided at one end of the lower case 26. As the driving hole 26a is fitted into a protrusion (not shown) of the cartridge driving unit 101, the cartridge 200 may be moved horizontally.

The present invention is not limited to this. That is, in the cartridge 200, the lower case 26 may be coupled to the upper case 21 through the guide portion without the body 30, and thus the lower case 26 may be moved horizontally through the guide portion.

Figure 7:
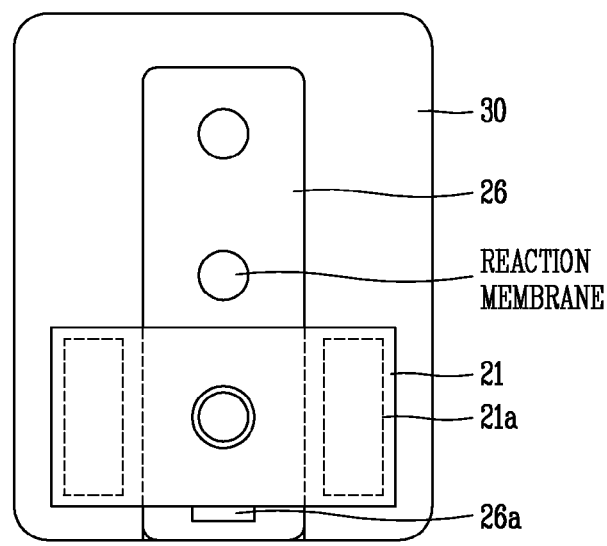
FIG. 7 is a planar view of a cartridge according to a first embodiment of the present invention.
Figure 7:
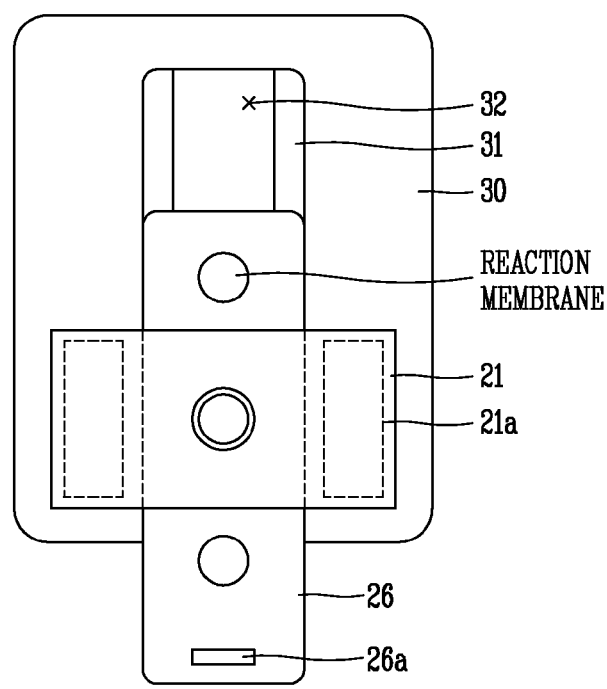

FIG. 7 is a planar view of the cartridge 200 according to a first embodiment of the present invention.

As shown in FIG. 6, once the cartridge 200 is mounted to the cartridge accommodation unit 100 of the apparatus for measuring cholesterol, membranes 22, 23 of the upper case 21 are aligned with rightmost membranes 24, 25 of the lower case 26 (first position).

Then, if the cartridge 200 is horizontally moved to the right by the cartridge driving unit 101, other membranes 24, 25 of the lower case 26 may be sequentially aligned with the membranes 22, 23 of the upper case 21 (second position, third position). Under an assumption that a moving speed of the cartridge 200 is constant, a horizontal moving distance is preset based on a distance between membranes of the lower case 26.

In the present invention, the first position or the third position may be set as a reference position for membrane alignment, under control of the controller 104.

Figure 8:
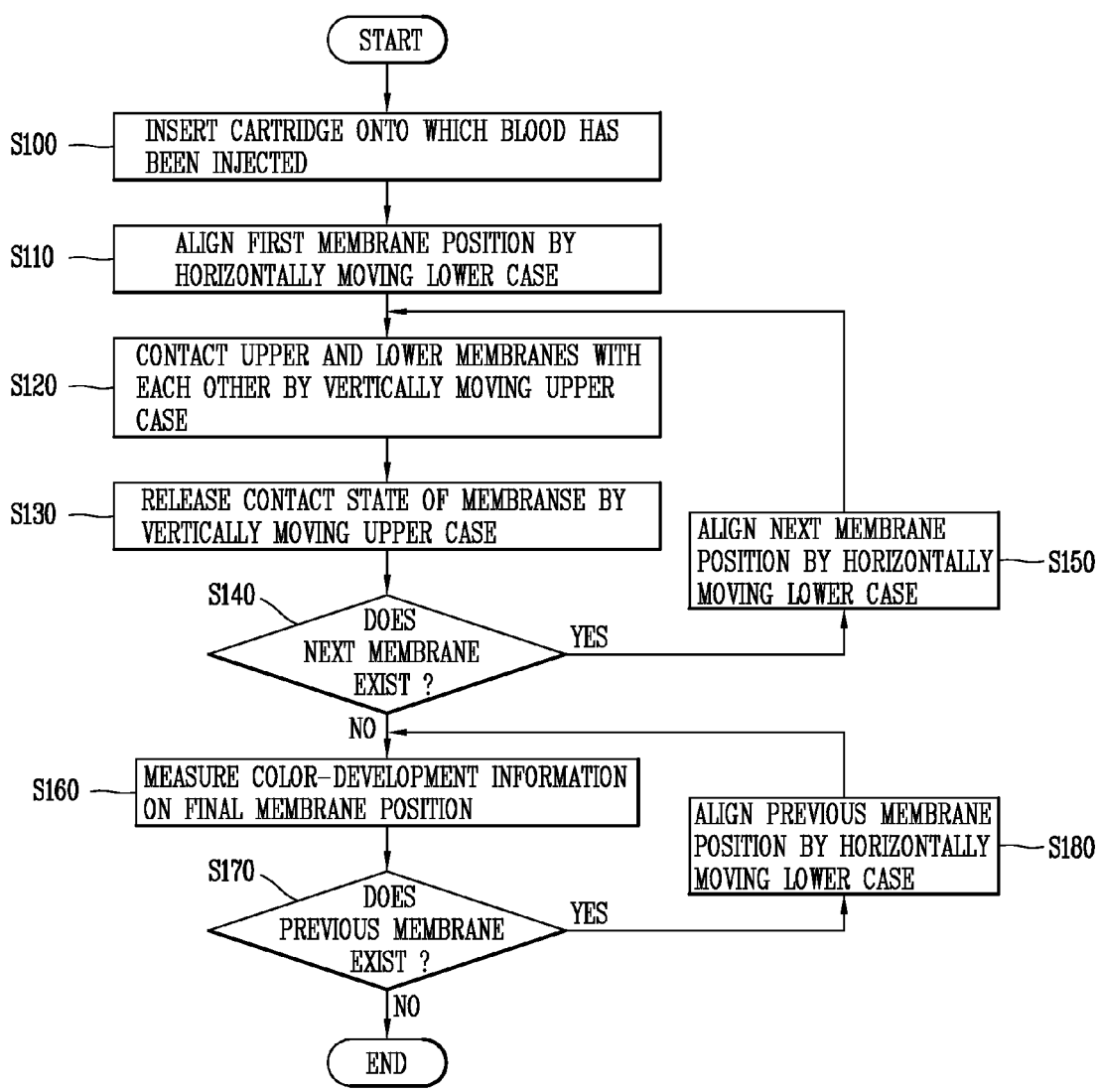
FIG. 8 is a flowchart illustrating a method of measuring cholesterol using a small amount of blood according to the present invention.

FIG. 8 is a flowchart illustrating a method of measuring cholesterol using a small amount of blood according to the present invention.

As shown in FIG. 8, a user mounts the cartridge 200 onto which blood has been injected, to the cartridge accommodation unit 100 of the apparatus for measuring cholesterol (S100). In this case, only serum is transferred to the spreading membrane 23, as red blood cells (RBCs) are filtered by the filtering membrane 22 of the cartridge 200.

The cartridge accommodation unit 100 may be implemented as an insertion type for inserting the cartridge by being provided at a lower surface or a side surface of the apparatus, or may be implemented as a mounting type including a cover at an upper part of the apparatus. The blood may be injected through a blood injection opening after the cartridge is firstly mounted to the cartridge accommodation unit 100.

The controller 104 may sense a mounted state of the cartridge, and when the cartridge is in an unstable state, the controller 104 may inform a user of the unstable state through the display unit 105 or an additional sound output module (not shown).

Once the cartridge 200 is mounted to the cartridge accommodation unit 100, the controller 104 checks positions and the number of membranes from the memory 103, based on a shape and a type of the cartridge 200. Then, the controller 104 generates a driving control signal based on the obtained information, thereby controlling the cartridge driving unit 101.

Firstly, the controller 104 may move the lower case 26 such that the membranes of the cartridge are aligned on the first position (S110). The first position, a reference position may be a position where the right membranes of the lower case 26 are aligned with the membranes of the upper case 21.

In another embodiment, the first position may be a position where the left membranes of the lower case 26 are aligned with the membranes of the upper case 21. The first position may be set by a user before measuring processes. The controller 104 controls the horizontal movement motor of the cartridge driving unit 101 according to the first position, thereby horizontally moving the lower case 26.

If the right membranes of the lower case 26 are aligned with the membranes of the upper case 21 on the first position, the controller 104 controls the vertical movement motor of the cartridge driving unit 101, thereby downward-vertically moving the upper case 21 to thus contact the membranes of the upper case 21 with the membranes of the lower case 26 (first contact) (S120). By the first contact, serum on the spreading membrane 23 of the upper case 21 is transferred to the reaction membrane 25 through the spreading membrane 24 of the lower case 26. The first contact is maintained for a preset time.

If the preset time for the first contact lapses, the controller 104 upward-vertically moves the upper case 21 by controlling the vertical movement motor, thereby releasing the first contact (S130).

Under this state, the controller 104 checks whether there is a next membrane to be contacted (S140). If there is a next membrane to be contacted, the controller 104 controls the horizontal movement motor again, thereby horizontally-moving the lower case 26 of the cartridge 200 to the next position (second position) for alignment (S150). On the other hand, if there is no next membrane to be contacted, the controller 104 checks a color-development reaction by immediately projecting light and completing the measuring processes (S160, S170).

In the present invention, three membranes are used, because membranes provided with a reaction layer with respect to three cholesterol measuring items, i.e., total cholesterol (TC), triglyceride (TG) and high-density lipoprotein (HDL) are used. Thus, the controller 104 may horizontally move the lower case 26 of the cartridge 200 to the next position (second position).

If middle membranes of the lower case 26 are aligned with the membranes of the upper case 21 on the second position, the controller 104 downward-vertically moves the upper case 21 to thus contact the membranes of the upper case 21 with the membranes of the lower case 26 (second contact) (S120). By the second contact, serum on the spreading membrane 23 of the upper case 21 is transferred to the reaction membrane 25 through the middle spreading membrane 24 of the lower case 26. The second contact is maintained for the same time as the preset time for the first contact.

If the preset time for the second contact lapses, the controller 104 upward-vertically moves the upper case 21, thereby releasing the second contact (S130). The controller 104 checks whether there is a next membrane to be contacted (S140). Since there is one membrane to be contacted, the controller 104 controls the horizontal movement motor again, thereby horizontally-moving the lower case 26 of the cartridge 200 to the next position (third position) for alignment (S150).

If the membranes of the upper case 21 are aligned with the left membranes of the lower case 26 on the third position, the controller 104 downward-vertically moves the upper case 21 to thus contact the membranes of the upper case 21 with the membranes of the lower case 26 (third contact) (S120).

Upon completion of the third contact on the third position, the controller 104 enters a step of measuring color-development information of the reaction membranes, because all the membrane contact processes are completed.

The step of measuring color-development information includes a series of processes of projecting light onto serum transferred to the reaction membranes 25 as a result of the first to third contacts, and detecting reflected light. The step of measuring color-development information starts from a position where the final contact has been released, i.e., a released state of the third contact.

Upon completion of the third contact, the controller 104 releases the third contact by upward-vertically moving the upper case 21, and then measures color-development information of the right reaction membrane 25 on the third position (first measurement). The color-development information is measured as light is projected onto the reaction membrane 25 from the LED of the measuring unit 102, and then light reflected from the reaction membrane 25 is received by the photo diode (PD).

Upon completion of the first measurement on the third position, the controller 104 checks whether there exists a reaction membrane (previous membrane) of which color-development information is to be measured (S170). If there is reaction membrane (previous membrane) of which color-development information is to be measured, the controller 104 horizontally moves the lower case 26 to the left, thereby aligning the membranes of the upper case 21 with the middle membranes of the lower case 26 (second position) (S180). Then, the controller 104 measures color-development information of the middle reaction membrane 25 on the second position (second measurement). On the other hand, if there is no reaction membrane (previous membrane) of which color-development information is to be measured, the controller 104 completes the step of measuring color-development information.

Upon completion of the second measurement on the second position, the controller 104 horizontally moves the lower case 26 to the left in the same manner as the first measurement, thereby aligning the membranes of the upper case 21 with the left membranes of the lower case 26 (first position) (S180). Then, the controller 104 measures color-development information of the left reaction membrane 25 on the first position (third measurement).

The controller 104 receives three color-development information of the reaction membranes 25 measured through the first to third measurements, from the measuring unit 102. Then, the controller 104 converts the color-development information into a concentration value of a reaction material by the concentration extraction module, thereby displaying, on the display unit 105, measurement results on cholesterol measurement items, i.e., total cholesterol (TC), triglyceride (TG), and high-density lipoprotein (HDL).

As aforementioned, in the present invention, serum (sample) of the upper case is transferred to the plurality of reaction membranes provided at the lower case, through membrane contact based on movement of the membranes of the upper case and the lower case, without an additional membrane path. Accordingly, a result value on concentration measurement may be obtained by using a small amount of blood.

Further, in the present invention, non-uniform serum distribution, deviation due to membranes, etc. may be removed through direct contact between the sample transferring membrane and the sample measuring membrane, and a membrane contact order, a membrane contact time, etc. may be controlled. This may allow a result value on concentration measurement more precise than the conventional one, to be obtained.

Figure 9:
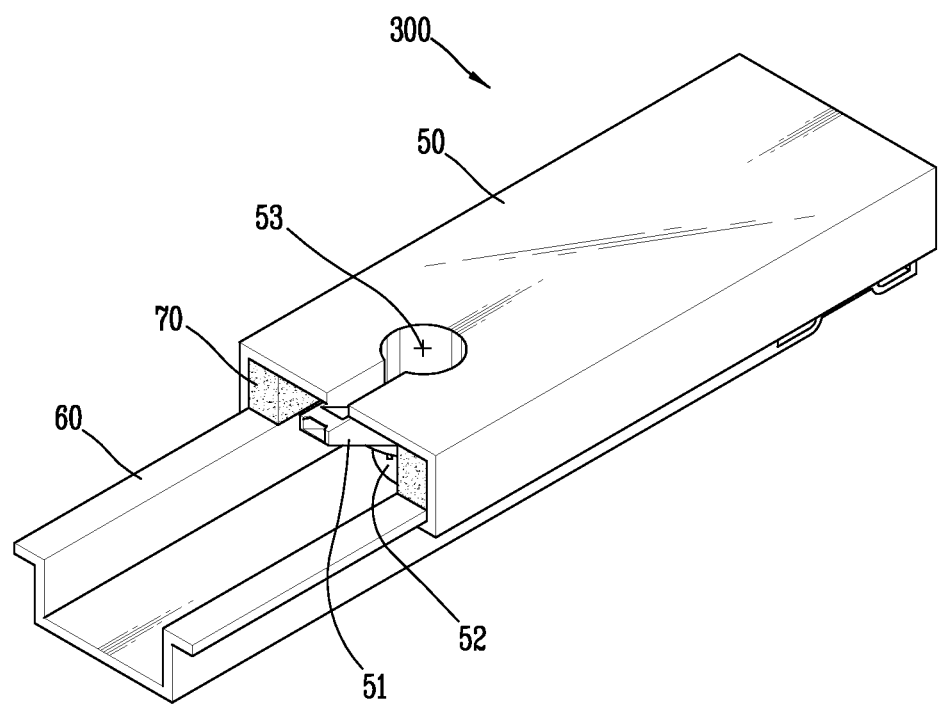
FIG. 9 is a configuration view of a cartridge according to a second embodiment of the present invention.
Figure 10:
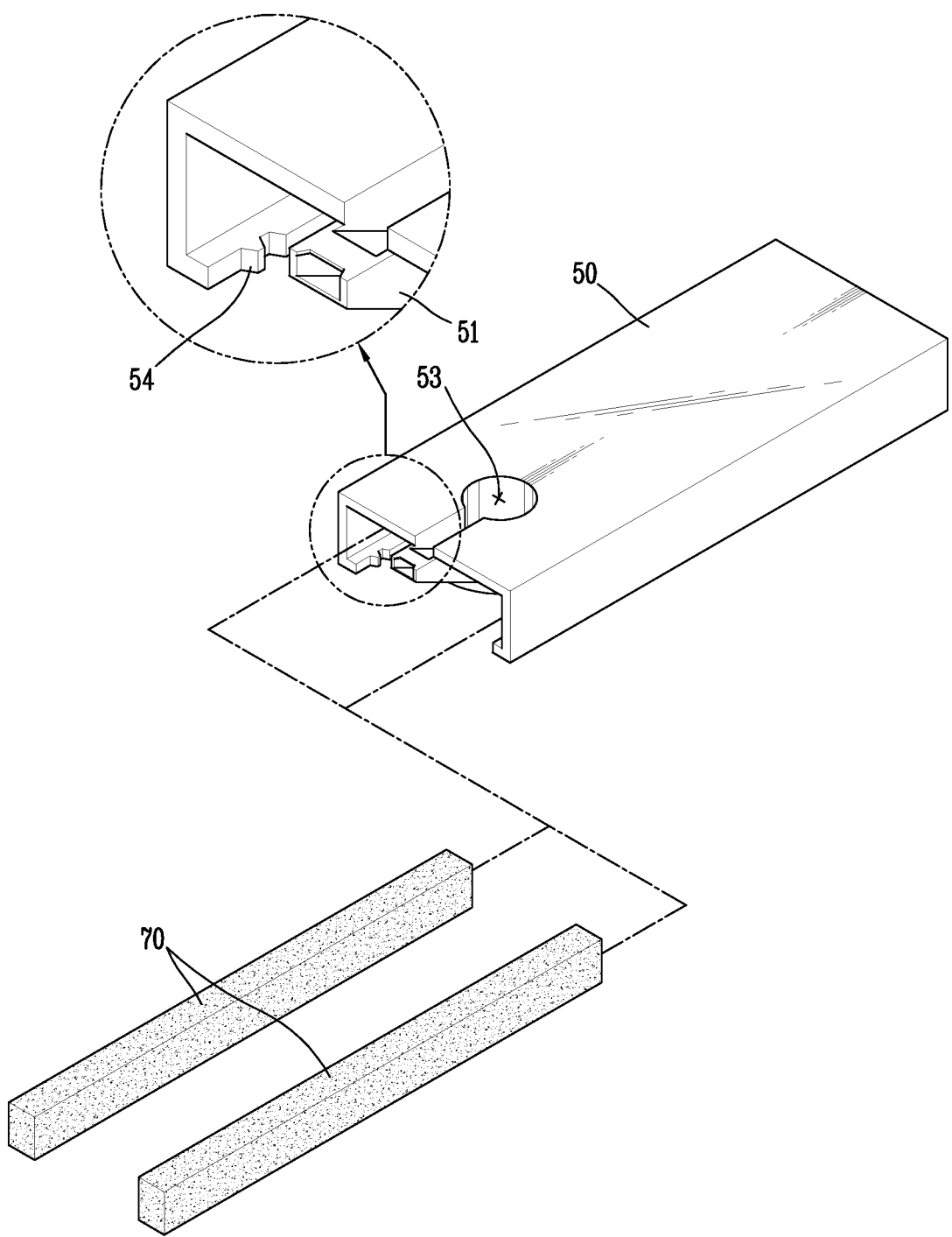
FIG. 10 is a disassembled perspective view of an upper case of a cartridge.

FIG. 9 is a configuration view of a cartridge 300 according to a second embodiment of the present invention, and FIG. 10 is a disassembled perspective view of an upper case 50 of the cartridge 300.

As shown in FIGS. 9 and 10, the cartridge 300 according to the second embodiment includes an upper case 50 having a pipe shape and forming a guide portion as a bottom surface thereof is cut into a predetermined size; an elastic member 70 spaced from the guide portion by a predetermined distance, and attached to an inner side of the upper case; and a drawer-type lower case 60 inserted to a space between the elastic member 70 and the guide portion, and sliding back and forth along the guide portion.

The upper case 50 includes at least one sample transferring membrane formed of the same material or different materials, and the lower case 60 includes at least one sample measuring membrane formed of the same material or different materials.

The at least one sample transferring membrane may be composed of a filtering membrane and a spreading membrane.

The upper case 50 and the lower case 60 may be formed of plastic resin.

The elastic member 70, configured to perform a buffering function, is inserted between the upper case 50 and the lower case 60. That is, the upper case 50 has "L"-shaped two sides, and is coupled to the lower case 60 which has "¬"-shaped two sides. Thus, the two sides of the upper case 50 operate as a guide portion.

The upper case 50 includes a blood injection member 51 configured to inject blood, a membrane accommodation portion 52 configured to accommodate therein a filtering membrane and a spreading membrane, and a cylindrical groove portion 53 through which a user views blood injected into the blood injection member 51 being injected into the filtering membrane of the membrane accommodation portion 52. A lower part of the groove portion 53 is connected to the blood injection member 51 and the membrane accommodation portion 52. One side of the groove portion 53 is cut along the blood injection member 51 so that blood transfer through the blood injection member 51 can be viewed.

A stopper 54, which has a groove portion and a protrusion portion, is provided at one end of the upper case 50. The stopper 54 is configured to restrict a horizontal movement range of the lower case 60.

Figure 11:
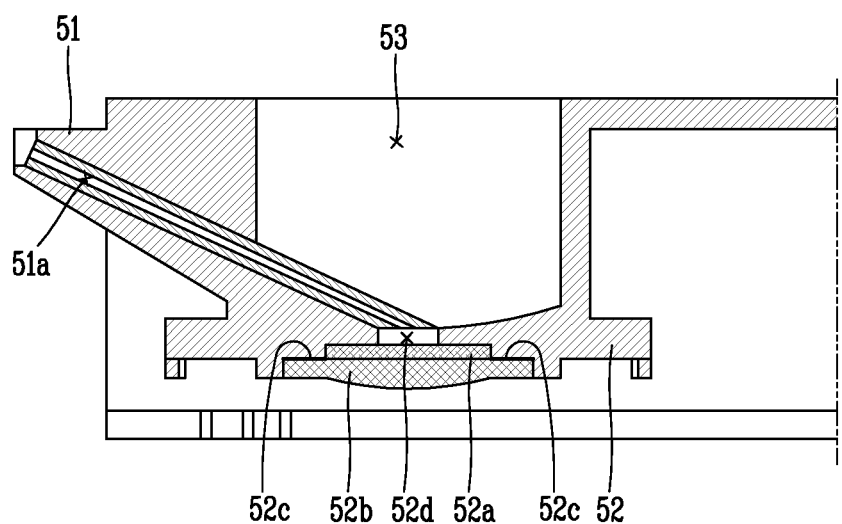
FIG. 11 is a sectional view of the upper case.
Figure 12A:
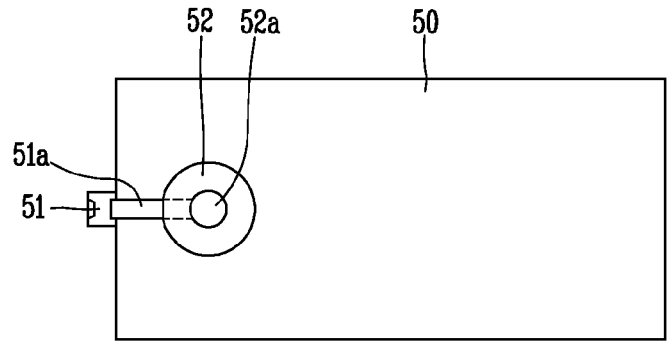
FIGS. 12A and 12B are a planar view and a bottom view of the upper case, respectively.
Figure 12B:
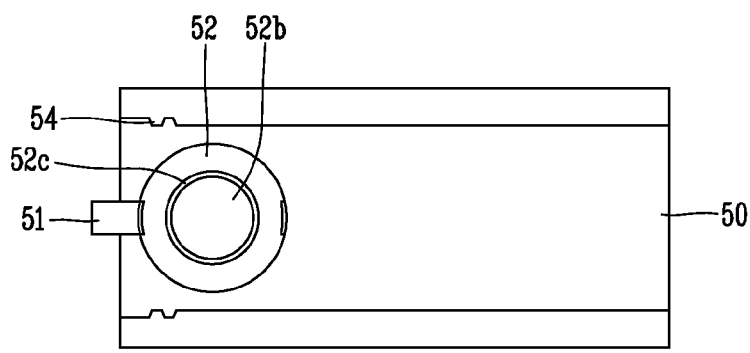

FIG. 11 is a sectional view of the upper case 11, and FIGS. 12A and 12B are a planar view and a bottom view of the upper case 11, respectively.

As shown in FIG. 11, the blood injection member 51 and the membrane accommodation portion 52 of the upper case 50 are integrally formed with each other.

One side of the blood injection member 51 protrudes from the upper case 50, and another side thereof is connected to the groove portion 53 and the membrane accommodation portion 52. The blood injection member 51 is formed of a transparent material, and provides a blood moving path. The blood injection member 51 is provided with a capillary channel 51*a* (or a blood transfer channel) for collecting a predetermined amount of blood.

The capillary channel 51*a* is formed to have a predetermined angle in a diagonal direction, and is configured to transfer blood to a membrane 52*a* by a capillary force of the capillary channel 51*a*, gravity, and an absorption force of the membrane.

The membrane accommodation portion 52 has a structure where multi-layer membranes 52*a*, 52*b* formed of the same material or different materials are bonded to each other by one-shot. The upper membrane 52*a* of the multi-layer membranes is inserted into a predetermined space of the membrane accommodation portion 52 formed of plastic resin. Edge parts 52*c* of the lower membrane 52*b* of the multi-layer membranes are welded to the membrane accommodation portion 52 by bonding energy such as heat or ultrasonic waves. In this case, a welding material is applied to one side of the membrane accommodation portion 52 to which the bonding energy is applied.

In an embodiment, the upper membrane 52a may be a filtering membrane for transferring serum by filtering red blood cells (RBCs) from blood which has been transferred through the capillary channel 51a. The lower membrane 52b may be a spreading membrane for spreading the transferred serum. The number of the upper membranes 52a may be increased according to an application field, and transfer of serum from the upper membrane 52a to the lower membrane 52b is performed by a capillary force and gravity.

Figure 13:
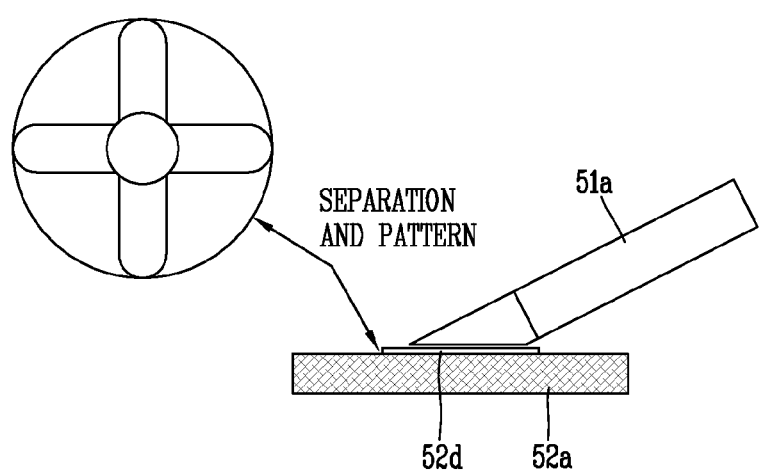
FIG. 13 is a view illustrating a pattern formed on a channel to which a membrane contacts.

FIG. 13 is a view illustrating a pattern formed on a channel where membranes contact each other.

Referring to FIG. 13, a pattern 52d of a '+' shape is formed at a contact part between the capillary channel 51a and the upper membrane 52a, and the channel 51a is spaced from the pattern 52d by a predetermined distance. Under such a configuration, blood can be transferred to a central part of each membrane, and blood can be uniformly absorbed to the membrane by the pattern.

If a user pricks his or her finger to discharge blood and then the user contacts the blood to an opening of the blood injection member 51 of the cartridge 300, the blood is downward transferred by a capillary force and gravity, along the capillary channel 51a. As shown in FIG. 12A, the user may check a blood transfer state through the groove portion 53, and may check whether a proper amount of blood has been transferred to the upper membrane 52a of the membrane accommodation portion 52.

The blood, which has been transferred by a capillary force and gravity, passes through the upper membrane 52a and the lower membrane 52b of the membrane accommodation portion 52, sequentially. As a result, red blood cells (RBCs) almost remain on the upper membrane 52a, and only serum is separated from the blood to thus be applied to the lower membrane 52b shown in FIG. 12B. If the same type of membrane as the upper membrane is additionally inserted, serum may be additionally separated from the blood through the membrane, for separation of only pure blood cells.

In the present invention, owing to the capillary channel having a predetermined gradient for transferring blood to the membranes, the conventional problem, i.e., a flow path of blood should be diverged to multiple steps for extraction of a desired component from blood, can be solved. Further, unlike in the conventional art, the air venting valve is not required, and blood leakage can be prevented.

Further, in the present invention, adopted is a multi-layer (or multi-stage) membrane structure for inserting the upper membrane into the membrane accommodation portion, and for bonding only the lower membrane 52b to one side of the membrane accommodation portion. This can solve the conventional problem that a membrane having a specific pore size should be fixed onto a backing plate and a membrane having a backing plate of multi-step should be fabricated, for implementation of multi-layer membranes.

In the present invention, since membranes presented on the market are combined with each other to implement membranes having a multi-layer structure, a structure of a cartridge can be simplified. Further, since multi-layer membranes formed of the same material or different materials are bonded to each other by one-shot, blood leakage can be prevented.

Figure 14:
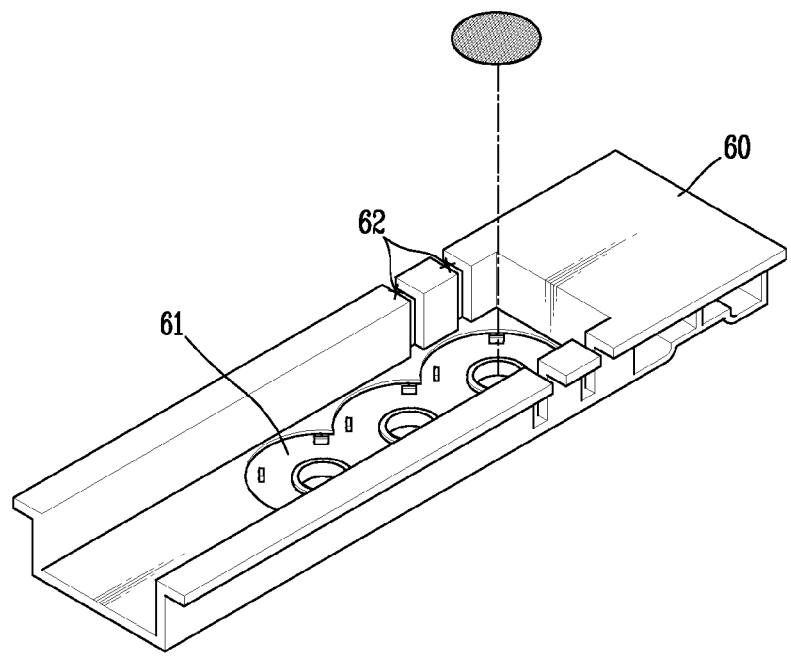
FIG. 14 is a configuration view of a lower membrane of a cartridge.
Figure 15:
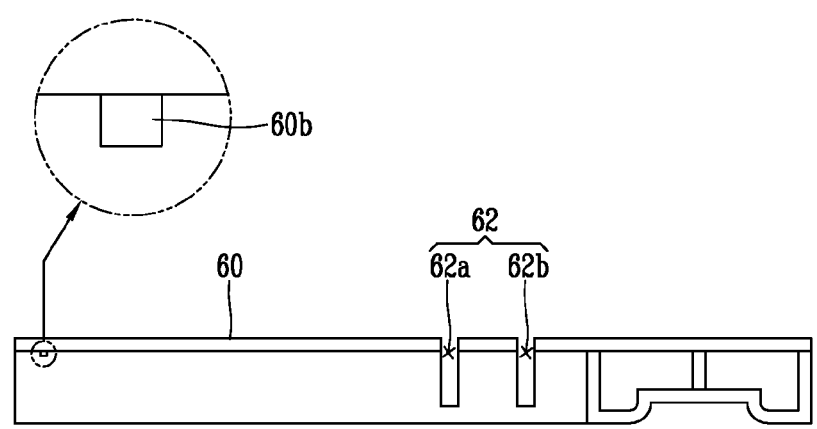
FIG. 15 is a side sectional view of the lower membrane of the cartridge.
Figure 16:
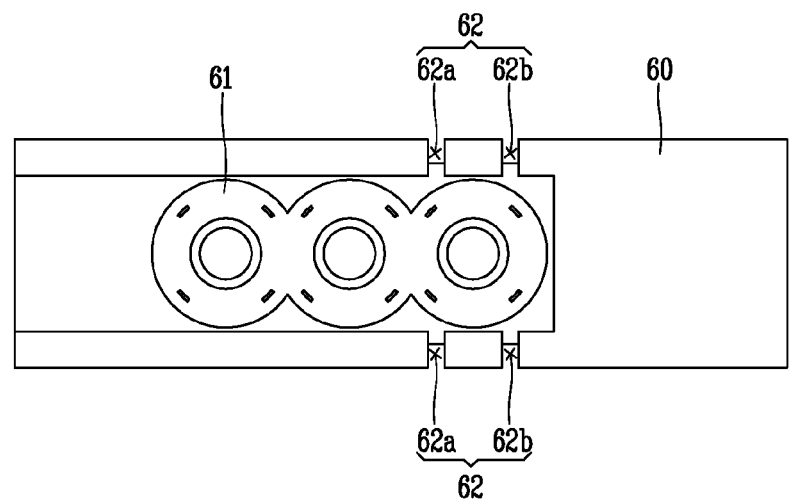
FIG. 16 is a planar view of the lower membrane.

FIG. 14 is a configuration view of a lower membrane of a cartridge. FIG. 15 is a side sectional view of the lower membrane of the cartridge. FIG. 16 is a planar view of the lower membrane.

As shown in FIGS. 14 to 16, a lower case 60 includes a membrane accommodation portion 61 configured to accommodate therein at least one membrane 60a, and a membrane mounting portion 62 configured to laminate a unit membrane on the membrane accommodation portion 61 in a floating manner. A protrusion portion 60b, which corresponds to the stopper 54 of the upper case 50, is provided on a side surface of the lower case 60. The protrusion portion 60b is configured to prevent the lower case 60 from being separated from the upper case 50 when the lower case 60 is moved out of the upper case 50 toward a first direction (e.g., a right direction of FIG. 15).

The membrane mounting portion 62 is composed of two cut-out portions 62a, 62b cut-out from two edges of the lower case 60 with a predetermined depth. A depth of each cut-output portion is deep enough for a corresponding membrane not to contact the membrane inside the membrane accommodation portion 61 when the corresponding membrane floats by a supporting member mounted to the membrane mounting portion 62. Further, the two cut-out portions 62a, 62b are spaced from each other.

The cut-out portion 62a is configured to restrict movement of the lower case 60 toward a second direction (e.g., a left direction of FIG. 15) by locking the lower case 60 by the stopper 54 of the upper case 50, when the lower case 60 is moved out of the upper case 50 toward the second direction. A position where the cut-out portion 62a is locked by the stopper 54, corresponds to a position where the membranes of the upper case 50 are aligned with the rightmost membranes of the membrane accommodation portion.

A structure of the membrane mounting portion 62 is not limited to a cut-out shape, but is variable according to a structure of the supporting member. For instance, when an end portion of the supporting member has a protruding shape, the membrane mounting portion 62 has a groove shape.

Figure 17:
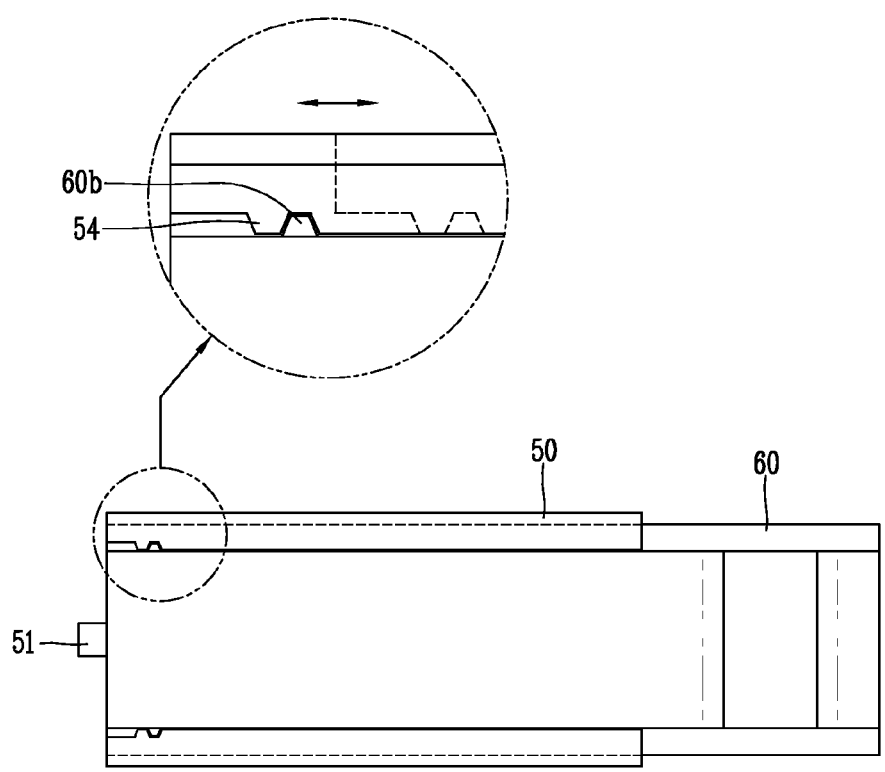
FIG. 17 is a bottom view illustrating a coupled state between an upper case and a lower case.

FIG. 17 is a bottom view illustrating a coupled state between the upper case 50 and the lower case 60.

As aforementioned, the protrusion portion 60b, which corresponds to the stopper 54 of the upper case 50, is provided on a side surface of the lower case 60. The protrusion portion 60b may be insertion-fixed to the groove portion of the stopper 54. Upon completion of blood collection, the cartridge is positioned in a cartridge accommodation unit (not shown) of the apparatus for measuring cholesterol, in a state where the protrusion portion 60b has been insertion-fixed to the groove portion of the stopper 54. The inserted state of the protrusion portion 60b into the groove portion of the stopper 54 is released when the upper case 50 is pressed by a motor of the apparatus for measuring cholesterol.

The present invention proposes a membrane laminating structure capable of minimizing errors and interference according to each step, and capable of actively controlling a corresponding step when necessary, by configuring consecutive reactions of blood as distribution reactions according to each step for each purpose. For this, the present invention proposes a membrane laminating structure having a floating structure.

Figure 18:
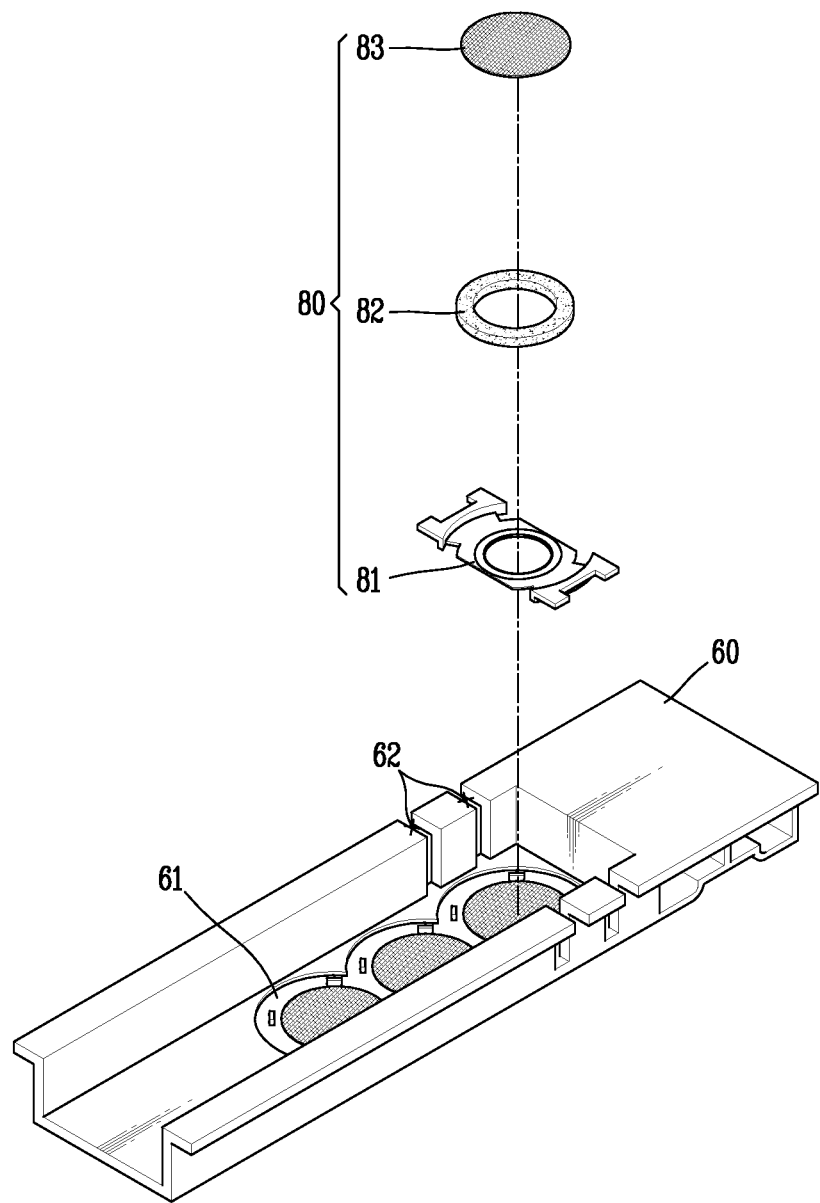
FIG. 18 is a view illustrating a unit membrane mounted to a membrane mounting portion.
Figure 19:
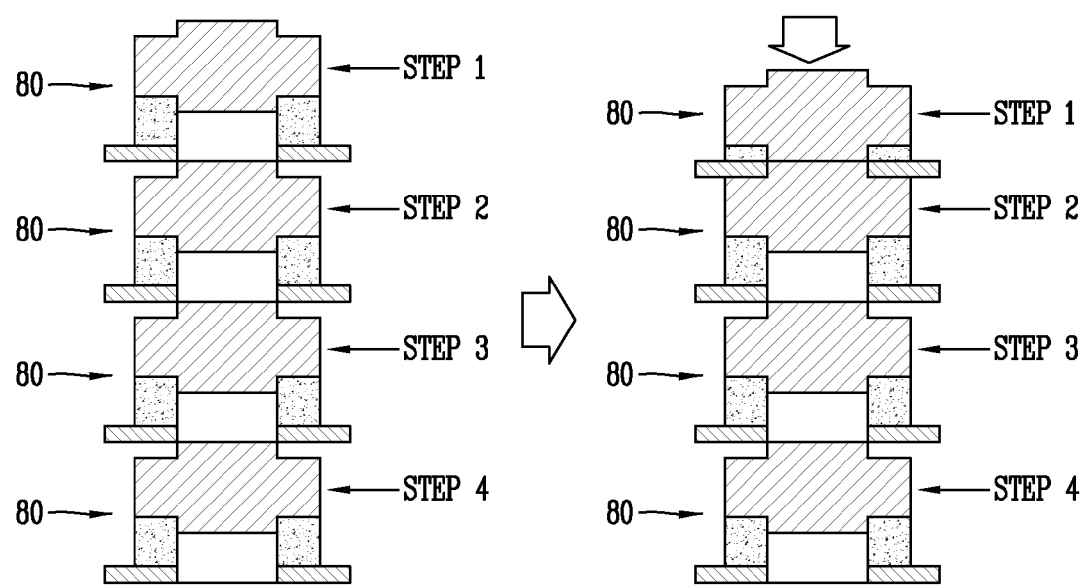
FIG. 19 is a view illustrating a concept to laminate unit membranes according to each reaction step.

FIG. 18 is a view illustrating a unit membrane mounted to the membrane mounting portion 62, and FIG. 19 is a view illustrating a concept to laminate unit membranes according to each reaction step.

As shown in FIG. 18, a plurality of unit membranes 80 may be mounted to the membrane mounting portion 62. The unit membrane 80 is composed of a supporting member 81, an elastic member 82 and a membrane 83. A single unit membrane corresponds to a single reaction step.

The supporting member 81 is formed of a rigid material, and the elastic member 82 and the membrane 83 are sequentially laminated on a central part of the supporting member 81. Two protrusion portions, which are mounted to the cut-out portions 62a, 62b of the membrane mounting portion 62, are formed at two sides of the supporting member 81. The supporting member 81 is formed such that its edge part is higher than its central part.

When the number of blood reaction steps is plural, a user may additionally laminate the unit membrane 80 according to each reaction step as shown in FIG. 19, thereby configuring entire reaction steps in a distributed manner. For instance, when connection between a first step and a second step among an entire reaction system is required, the upper case 50 is pressed with a predetermined strength, by the vertical movement motor. As a result, the elastic member 82 is compressed to connect two membranes to each other. Accordingly, the first step and the second step of blood reactions can be consecutively performed. A driving strength of the vertical movement motor according to the number of the unit membranes 80 is stored in the memory 103. That is, in the present invention, the floating type of unit membrane is laminated according to each reaction step, and then the upper case 50 is pressed with a predetermined strength by the vertical movement motor. Under such a configuration, blood reaction processes can be performed in a consecutive manner or in a non-consecutive manner.

In the present invention, efficiency and performance of the apparatus for measuring cholesterol can be enhanced, since consecutive processes on a micro fluid chip can be variously driven in active and distributed manners.

Figure 20A:
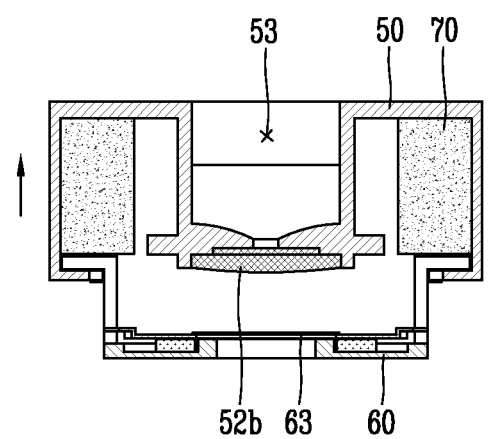
FIGS. 20A and 20B are views illustrating an operation to transfer serum separated from an upper case by vertically transferring the upper case, to membranes of a lower case.
Figure 20B:
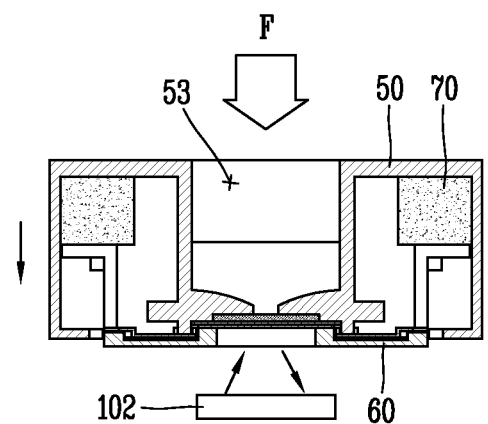

FIGS. 20A and 20B are views illustrating an operation to transfer serum separated from the upper case by vertically transferring the upper case, to the membranes of the lower case.

As shown in FIGS. 20A and 20B, like in the first embodiment, the controller 104 horizontally moves the lower case 60 by controlling the cartridge driving unit 101, thereby aligning the membrane of the upper case 50 with each membrane of the lower case 60. Then, the controller 104 vertically moves the upper case 50, thereby contacting the membranes of the upper case 50 with the membranes of the lower case 60. If a predetermined number of unit membranes 80 are laminated on the lower case 60, the controller 104 may control a driving strength of the vertical movement motor based on the number of the laminated unit membranes. As a result, serum separated from the spreading membrane of the upper case 50 is transferred to the membrane of the lower case 60, directly or through the predetermined number of unit membranes 80. If serum included in the membrane of the upper case 50 is transferred to the reaction membrane of the lower case 60 through the membrane contact, or through the spreading membrane, the controller 104 upwardly-vertically moves the upper case 50 by controlling the vertical movement motor of the cartridge driving unit 101, thereby releasing the membrane contact.

The controller 104 repeatedly performs membrane contact by moving the upper case 50 and the lower case 60. Once serum is transferred to all the reaction membranes of the lower case 60 as the membrane contact is completed, the controller 104 projects light onto the reaction membranes by controlling the measuring unit 102, thereby measuring color-development information. Then, the controller 104 measures a cholesterol level based on the measured color-development information, and displays the measured cholesterol level on the display unit 105. The step of measuring color-development information is performed in opposite order to the membrane contact step.

As aforementioned, in the present invention, the upper case including membranes is moved vertically, and the lower case including membranes is moved horizontally, thereby aligning and contacting the membranes with each other. As a result, fluid loss due to fluid flow can be prevented, and thus a desired measurement result can be obtained by using even a small amount of blood.

Further, membranes are aligned and contacted with each other as the upper case including the membranes is moved vertically, and the lower case including the membranes are moved horizontally. As a result, non-uniform distribution of serum can be prevented, a membrane contact time can be controlled, and a more precise result value on concentration measurement can be obtained.

Further, in the present invention, a capillary channel having a predetermined gradient for transferring blood to membranes is provided. As a result, the conventional problem, i.e., a flow path of blood should be diverged through multiple steps for extraction of desired components from blood, can be solved, and blood leakage can be prevented.

In the present invention, efficiency and performance of the apparatus for measuring cholesterol can be enhanced, since consecutive processes on a micro fluid chip can be driven in various active and distributed manners.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An apparatus for measuring cholesterol comprising:
   a cartridge including:
   an upper case having a sample transferring membrane; and
   a lower case having a sample measuring membrane at at least one alignment position, the upper case being movably coupled to the lower case;
   a cartridge accommodation unit configured to accommodate the cartridge therein;
   a memory configured to store therein setting information for sample measurement; and
   a controller configured to:
   align the sample transferring membrane of the upper case and the at least one sample measuring membrane by horizontally moving the lower case of the cartridge, according to the stored setting information and
   contact the sample transferring membrane of the upper case and the at least one sample measuring membrane with each other by vertically moving the upper case for sample transfer at the at least one alignment position.

2. The apparatus of claim 1, wherein the setting information includes a membrane initial alignment position, a membrane contact time, cholesterol measuring items, horizontal moving distances of the lower case, vertical moving distance of the upper case, and a vertical moving strength of the upper case.

3. The apparatus of claim 1, wherein the sample transferring membrane is a multi-layer membrane, and
wherein the sample measuring membrane includes a reaction membrane.

4. The apparatus of claim 3, wherein the multi-layer membrane is composed of at least one filtering membrane and one spreading membrane,
wherein the filtering membrane is inserted into a membrane accommodation portion of the upper case, and
wherein an edge of the spreading membrane is welded to a predetermined region of the membrane accommodation portion.

5. The apparatus of claim 1, wherein the cartridge further comprises a body having a plate-shape, the body including a guide portion of a predetermined depth,
wherein the lower case is inserted into the guide portion, the guide portion and the lower casing having a same shape, and
wherein the upper case crosses the lower case above the lower case, the upper case having opposite sides fixed to the body by an elastic member.

6. The apparatus of claim 5, wherein the at least one alignment position includes an outermost position, and
wherein, when the lower case is completely inserted into the body, the sample transferring membrane of the upper case is automatically aligned with the sample measuring membrane at the outermost position.

7. The apparatus of claim 1, further comprising:
a measuring unit configured to detect color-development information by outputting an optical signal to the sample measuring membrane; and
a display unit,
wherein the controller outputs result values on cholesterol measurement to the display unit by processing the color-development information detected by the measuring unit.

8. The apparatus of claim 1, wherein the upper case has a pipe shape that defines a guide portion,
wherein the cartridge includes an elastic member spaced from the guide portion, and attached to an inner side of the upper case, and
wherein the lower case is formed as a drawer inserted into a space between the elastic member and the guide portion, the drawer being slidable back and forth along the guide portion.

9. The apparatus of claim 8, wherein the upper case includes:
a blood injection member configured to inject blood;
a membrane accommodation portion configured to accommodate therein the sample transferring membrane, the sample transferring membrane including a filtering membrane and a spreading membrane; and
a cylindrical groove portion through which a user can view blood injected by the blood injection member into the filtering membrane in the membrane accommodation portion.

10. The apparatus of claim 9, wherein the blood injection member, the membrane accommodation portion, and the groove portion are integrally connected to one another.

11. The apparatus of claim 9, wherein one side of the groove portion is cut such that blood transfer from the blood injection member to the membrane accommodation portion is viewable.

12. The apparatus of claim 9, wherein the blood injection member is formed of a transparent material and includes a blood transfer channel configured to transfer blood to the sample transferring membrane in the membrane accommodation portion, the blood transfer channel being inclined at a predetermined angle with respect to the membrane accommodation portion.

13. The apparatus of claim 12, wherein the blood transfer channel is spaced from the sample transferring membrane in the membrane accommodation portion, and
wherein a predetermined pattern for blood distribution is formed on a surface of the sample transferring membrane in the membrane accommodation portion.

14. The apparatus of claim 9, wherein the sample transferring membrane is a multi-layer membrane,
wherein an upper membrane of the multi-layer membranes is inserted into a predetermined space of the membrane accommodation portion, and
wherein edge parts of a lower membrane of the multi-layer membranes are welded to the membrane accommodation portion.

15. The apparatus of claim 8, wherein the at least one sample membrane is provided as a unit membrane, and
wherein the lower case includes:
a membrane accommodation portion configured to accommodate therein the unit membrane on a bottom surface thereof; and
a membrane mounting portion provided on a side surface of the lower case and configured to laminate a plurality of unit membranes on the membrane accommodation portion in a floating manner, and
wherein the membrane mounting portion includes a cut-out portion or a groove portion for fixing an edge of the unit membrane.

16. The apparatus of claim 15, wherein each unit membrane includes:
a supporting member having an edge thereof fixable to the membrane mounting portion;
an elastic member disposed on the supporting member; and
the at least one sample measuring membrane disposed on the elastic member.

17. A method of measuring cholesterol using a cartridge including an upper case having at least one sample transferring membrane and a lower case having a sample measuring membrane located at at least one alignment position, the method comprising:
mounting a cartridge, onto which a sample to be measured has been injected, to a cartridge accommodating unit;
sequentially-aligning the at least one sample transferring membrane and the sample measuring membrane with each other by horizontally moving the lower case according to setting information;
contacting the at least one sample transferring membrane and the sample measuring membrane with each other by vertically moving the upper case to transfer the sample to be measured at the at least one alignment position;
measuring color-development information by projecting light onto the sample measuring membrane while horizontally moving the lower case in a state where the contact state of the membranes has been released; and
calculating a cholesterol level by analyzing the measured color-development information.

18. The method of claim 17, wherein the sample transferring membrane is composed of a filtering membrane and a spreading membrane, and
wherein the sample measuring membrane is composed of a spreading membrane and a reaction membrane.

19. The method of claim 17, wherein the setting information includes a membrane initial alignment position, a membrane contact time, cholesterol measuring items, horizontal moving distances of the lower case, vertical moving distance of the upper case and a vertical moving strength of the upper case.

20. The method of claim 17, wherein the at least one alignment position includes a first alignment position and a second alignment position, and wherein the step of contacting the at least one sample transferring membrane and the sample measuring membrane at the at least one alignment position with each other includes:

aligning the sample measuring membrane at the first alignment position with the sample transferring membrane of the upper case by horizontally moving the lower case;

contacting the sample transferring membrane and the sample measuring membrane at the first alignment position for a predetermined time by downwardly moving the upper case;

releasing the contact state of the sample transferring membrane and the sample measuring membrane at the first alignment position by upwardly moving the upper case after a predetermined time lapses; and aligning the sample measuring membrane at the second alignment position with the sample transferring membrane by horizontally moving the lower case.

* * * * *